United States Patent
Akada et al.

(10) Patent No.: US 8,633,029 B2
(45) Date of Patent: Jan. 21, 2014

(54) AGENT FOR IMPROVING GENE TRANSFER EFFICIENCY TO MAMMALIAN CELLS

(75) Inventors: Rinji Akada, Yamaguchi (JP); Mikiko Nakamura, Yamaguchi (JP)

(73) Assignee: Yamaguchi University, Yamaguchi (JP)

( * ) Notice: Subject to any disclaimer, the term of this patent is extended or adjusted under 35 U.S.C. 154(b) by 0 days.

(21) Appl. No.: 13/583,847

(22) PCT Filed: Mar. 13, 2011

(86) PCT No.: PCT/JP2011/001449
§ 371 (c)(1),
(2), (4) Date: Sep. 10, 2012

(87) PCT Pub. No.: WO2011/114678
PCT Pub. Date: Sep. 22, 2011

(65) Prior Publication Data
US 2013/0005041 A1    Jan. 3, 2013

(30) Foreign Application Priority Data

Mar. 15, 2010  (JP) ................................. 2010-057732

(51) Int. Cl.
*C12N 15/88*  (2006.01)
*C09K 3/00*  (2006.01)

(52) U.S. Cl.
USPC ....................................... 435/458; 252/182.3

(58) Field of Classification Search
None
See application file for complete search history.

(56) References Cited

U.S. PATENT DOCUMENTS 4,650,909 A * 3/1987 Yoakum ........................ 568/621

FOREIGN PATENT DOCUMENTS

| JP | 2005269920 | 10/2005 |
| JP | 2009195197 | 9/2009 |
| WO | WO03087384 A1 * | 10/2003 |
| WO | 2006122828 A2 | 11/2006 |
| WO | 2007046356 A1 | 4/2007 |

OTHER PUBLICATIONS

Jacobsen et al. Methods, Transfection of Mammalian Cells, vol. 33, Issue 2, Jun. 2004, pp. 104-112.*
Duchler, M., et al., "Transfection of epithelial cells is enhanced by combined treatment with mannitol and polyethyleneglycol," The Journal of Gene Medicine (2001), 3:115-124.
Geslain, R., et al., "Functional Analysis of Human tRNA Isodecoders," J. Mio. Biol. (2010), 396:821-831.
Tseng, WC, et al. "Effects of Enhancers and Coating Substrates on the Transgene Expression Mediated by Branched Polyethylenimine," Journal of Applied Polymer Science (2009), 114:2221-2225.
Zaitsev, S., et al., "Polyelectrolyte Nanoparticles Mediate Vascular Gene Delivery," Pharmaceutical Research (2004) 21:9, 1656.
Koumbi, D., et al., "Detailed Studies on the Mechanism and Factors Mediating Lipofection Potency of Cationic Phosphonolipid-based Gene Transfer into Human Cells," Blood Cells, Molecules and Diseases (2008) vol. 40, No. 2, pp. 272-273.
Jung, H.J., et al., "Carassius auratus-originated recombinant histone H1C-terminal peptide as gene delivery material," Biotechnology progress (2008) vol. 24, No. 1 pp. 17-22.
Chabaud, P., et al., "Cationic nucleoside lipids for gene delivery," Bioconjugate chemistry (2006) vol. 17, No. 2, pp. 466-472.
Nimesh, S., et al., "Polythylenimine nanoparticles as efficient transfecting agents for mammalian cells," Journal of controlled release (2008) vol. 110, No. 2, pp. 457-468.
EP 11755871.8 Extended European Search Report dated Sep. 2, 2013.

* cited by examiner

*Primary Examiner* — Janet Epps-Smith
(74) *Attorney, Agent, or Firm* — Chainey P. Singleton; Edwin S. Flores; Chalker Flores, LLP (57) ABSTRACT

Provided is an efficiency improving agent for gene transfer to mammalian cells, a method for improving efficiency of gene transfer to mammalian cells, and a method for transforming mammalian cells. The method is characterized in that tRNA is used in combination with a lipofection reagent. Preferably, the agent may be used so that the tRNA concentration in a lipofection solution falls within the range of 3 to 50 µg/mL, and the concentration in a culture is approximately 1/10. More preferably, tRNA and PEG may be used in combination with a lipofection reagent. According to the present invention, gene transfer to mammalian cells with high efficiency can be achieved.

5 Claims, 5 Drawing Sheets

AGENT FOR IMPROVING GENE TRANSFER EFFICIENCY TO MAMMALIAN CELLS

TECHNICAL FIELD

The present invention relates to an efficiency improving agent for gene transfer to mammalian cells, a method for improving efficiency of gene transfer to mammalian cells, and a method for transforming mammalian cells.

BACKGROUND ART

Various methods for gene transfer to cells are known. For example, a method using a virus vector, a method using a specific receptor, or a cell fusion method is known as a biological method; a microinjection method, an electroporation method, a gene gun method, or an ultrasound-mediated gene transfer method is known as a physical method; and a calcium phosphate coprecipitation method, a liposome method, a lipofection method, a DEAE dextran method, or an alkali metal method is known as a chemical method. The lipofection method is a method which involves forming a liposome-DNA complex by the electric interaction between a lipid bilayer membrane vesicle consisting of a positively charged lipid or the like (liposome) and DNA to be transferred and incorporating the complex into host cells by phagocytosis or membrane fusion. The lipofection method is distinguished from the liposome method in that DNA is not necessarily encapsulated in the liposome. Generally, when gene transfer is carried out, the lipofection method is first performed due to its simplicity. The lipofection method is relatively widely used because it has the merit of having high versatility and simplicity and being suitable for the treatment of many samples. However, the lipofection method also has the demerit of being inferior to the electroporation method or the method using a virus vector in terms of gene transfer efficiency. The method using a virus vector has the merit of having high gene transfer efficiency, but has, for example, problems of 1) it taking a time of as much as about 1 week until a target gene is placed in a virus vector, followed by transferring the virus vector to virus-producing cells, then producing viruses containing the target gene, and infecting cells with the viruses, 2) requiring facilities for handling a virus vector, 3) requiring technical personnel sufficiently skilled for handling a virus vector, and 4) sometimes inserting the virus vector into the somatic genome and leaving it there. Thus, if a method can be developed for efficiently transferring a gene without using a virus vector, it represents a useful method.

The present inventors have been hitherto studying for improving efficiency of gene transfer to yeast. For example, Patent Document 1 describes a method for transforming yeast, comprising directly mixing a yeast culture with a solution containing DNA to be transferred to the yeast cells, an alkali metal ion, and polyethylene glycol (PEG) for transformation. Patent Document 1 also describes the further use of carrier DNA or carrier RNA in the above mixed solution. However, the method of the Patent Document 1 is a method for yeast cells and based on an alkaline metal method. The method of the present invention is entirely different from the method of Patent Document 1 because it is a method for mammalian cells and based on the lipofection method. In addition, Patent Document 1 teaches nothing about tRNA. Because yeast cells have cell walls, the lipofection method is not commonly used.

Incidentally, Patent Document 2 describes a transformation method having a high gene transfer efficiency, using mammalian cells as host cells. The transformation method of Patent Document 2 is characterized by simultaneously transferring a first vector comprising a mammalian replication initiation region and a mammalian nuclear matrix association region and a second vector comprising a promoter functioning in mammalian cells and a target gene encoding a secretory protein to mammalian cells so that the mole ratio of the first vector to the second vector ranges from 0.3 to 5. Patent Documents 1 and 2 also disclose that the use of a polyethylene glycol having a particular molecular weight improves gene transfer efficiency. However, both documents teach nothing about the use of tRNA in gene transfer to mammalian cells.

PRIOR ART DOCUMENTS

Patent Documents

Patent Document 1
Japanese Unexamined Patent Application Publication No. 2005-269920
Patent Document 2
Japanese Unexamined Patent Application Publication No. 2009-195197

Non-Patent Documents

Non-patent Document 1
Journal of Applied Polymer Science, 114, 2221-2225, 2009
Non-patent Document 2
The Journal of Gene Medicine, 3, 115-124, 2001

SUMMARY OF THE INVENTION

Object to be Solved by the Invention

An object of the present invention is to provide an efficiency improving agent for gene transfer to mammalian cells, a method for improving efficiency of gene transfer to mammalian cells, and a method for transforming mammalian cells.

Means to Solve the Object

To improve efficiency of gene transfer to mammalian cells by a lipofection method, the present inventors investigated optimal conditions for the concentration of the transgene, the concentration of a lipofection reagent, the number of host cells, and the like, but failed to make significant improvement in efficiency of gene transfer. As a result of further intensive studies, the present inventors have found that tRNA can be used in combination with a lipofection reagent to prominently improve efficiency of gene transfer to mammalian cells, thereby accomplishing the present invention.

Thus, the present invention relates to (1) an efficiency improving agent for gene transfer to mammalian cells, wherein the agent comprises tRNA and is used in combination with a lipofection reagent; (2) an efficiency improving agent for gene transfer to mammalian cells, comprising tRNA and a lipofection reagent; (3) the improving agent according to (1) or (2) above, wherein the agent is used so that the concentration of tRNA in a lipofection solution ranges from 3 to 50 µg/mL; (4) the improving agent according to any one of (1) to (3) above, wherein the agent is further used in combination with polyethylene glycol; (5) the improving agent according to any one of (1) to (4) above, wherein the polyethylene glycol has a molecular weight ranging from 2,000 to 6,000; (6) the improving agent according to any one of (1) to (4) above, wherein the polyethylene glycol has a molecular weight ranging from 3,000 to 5,000; and (7) the improving agent according to any one of (1) to (6) above, wherein the mammal is a mammal selected from the group consisting of a human, a mouse, and a monkey.

The present invention also relates to (8) a method for improving efficiency of gene transfer to mammalian cells, wherein tRNA is used in combination with a lipofection reagent; and (9) a method for transforming mammalian cells, comprising lipofecting a target gene into mammalian cells by using tRNA in combination with a lipofection reagent.

Effect of the Invention

According to the efficiency improving agent for gene transfer and the method for improving efficiency of gene transfer of the present invention, efficiency of gene transfer to mammalian cells can be prominently improved. According to the method for transforming mammalian cells of the present invention, mammalian cells can be transformed with high efficiency.

MODE OF CARRYING OUT THE INVENTION

1. Efficiency Improving Agent for Gene Transfer to Mammalian Cell of Present Invention The efficiency improving agent for gene transfer to mammalian cells of the present invention (hereinafter, also indicated as "the improving agent of the present invention") is characterized by comprising tRNA and being used in combination with a lipofection reagent. The tRNA-containing improving agent of the present invention can be used in combination with a lipofection reagent to prominently improve efficiency of gene transfer to mammalian cells. The effect capable of improving efficiency of gene transfer to mammalian cells when lipofection is performed in combination with the lipofection reagent is herein also indicated as "the gene transfer efficiency-improving effect of the present invention". The action mechanism of the gene transfer efficiency-improving effect of the present invention is uncertain, but the use of tRNA in combination with the lipofection reagent probably improves the gene incorporation efficiency into mammalian cells.

As used herein, the "tRNA" is not particularly limited provided that it is a tRNA having the gene transfer efficiency-improving effect of the present invention, and can be preferably exemplified by calf liver (Bovine)-derived tRNA (for example, leucine tRNA consisting of the sequence described in SEQ ID NO: 1), yeast (*Saccharomyces cerevisiae*)-derived tRNA (for example, leucine tRNA consisting of the sequence described in SEQ ID NO: 2), wheat germ (Wheat)-derived tRNA (for example, phenylalanine tRNA consisting of the sequence described in SEQ ID NO: 3), and *E. coli*-derived tRNA (for example, leucine tRNA consisting of the sequence described in SEQ ID NO: 4) and among others, can be more preferably exemplified by the yeast-derived tRNA because it has a high degree of the gene transfer efficiency-improving effect of the present invention.

As used herein, the "tRNA" also encompasses a mutant of tRNA (hereinafter simply indicated as "tRNA mutant") as long as the mutant has the gene transfer efficiency-improving effect of the present invention. The tRNA mutant means a polyribonucleotide which is a mutant of the polyribonucleotide shown in any of SEQ ID NOs: 1 to 4 and has the gene transfer efficiency-improving effect of the present invention in any mammalian cells.

Such tRNA mutants include:

(a) a polyribonucleotide having 80% or more, preferably 85% or more, more preferably 90% or more, still more preferably 95% or more, most preferably 98% or more identity to the polyribonucleotide shown in any of SEQ ID NOs: 1 to 4 and having the gene transfer efficiency-improving effect of the present invention in any mammalian cells;

(b) a polyribonucleotide consisting of a polyribonucleotide in which 1 or more ribonucleotides are deleted, substituted, or added in the polyribonucleotide shown in any of SEQ ID NOs: 1 to 4 and having the gene transfer efficiency-improving effect of the present invention in any mammalian cells; and (c) a polyribonucleotide capable of hybridizing with a polynucleotide complementary to the polyribonucleotide shown in any of SEQ ID NOs: 1 to 4 under stringent conditions and having the gene transfer efficiency-improving effect of the present invention in any mammalian cells.

The "polyribonucleotide in which 1 or more ribonucleotides are deleted, substituted, or added" in (b) above means a polyribonucleotide in which any number of, for example 1 to 20, preferably 1 to 15, more preferably 1 to 10, still more preferably 1 to 5, especially 1 to 3, ribonucleotides are deleted, substituted, or added.

The "under stringent conditions" in (c) above refers to conditions under which a so-called specific hybrid is formed and a non-specific hybrid is not formed, and specific examples thereof can include conditions under which DNAs (or DNA and RNA) having 80% or more, preferably 85% or more identity to each other hybridize with each other and DNAs (or DNA and RNA) having identity lower than the above range to each other do not hybridize with each other, or conditions under which such hybridization occurs at a salt concentration corresponding to 1×SSC solution (the composition of SSC solution with a one-time concentration consists of 150 mM sodium chloride and 15 mM sodium citrate) and 0.1% SDS or 0.1×SSC and 0.1% SDS at 65° C. as typical washing conditions for Southern hybridization. The hybridization can be performed according to a method as described in Molecular Cloning 2nd. ed. or the like. Examples of the "polyribonucleotide capable of hybridization under stringent conditions" in (c) above can include a polyribonucleotide having a certain level or more of identity to the polynucleotide used as a probe, and such a polyribonucleotide can be preferably exemplified by a polyribonucleotide having 80% or more, preferably 85% or more, more preferably 90% or more, still more preferably 95% or more, most preferably 98% or more identity thereto.

The polyribonucleotide shown in any of SEQ ID NOs: 1 to 4 above can be prepared by any method known to those skilled in the art such as a chemical synthesis method or a genetic engineering technique using RNA polymerase.

The above-described mutant of the polyribonucleotide can also be prepared by any method known to those skilled in the art such as a chemical synthesis method, a genetic engineering technique, or mutagenesis. Specifically, the polyribonucleotide mutant can be obtained by introducing mutation into the polyribonucleotide shown in any of SEQ ID NOs: 1 to 4 using a method involving contacting an agent serving as a mutagen with the polyribonucleotide, a method involving the irradiation thereof with ultraviolet rays, a genetic engineering technique, or the like. A site-directed mutagenesis method as a genetic engineering technique is useful because it is a technique capable of introducing a certain mutation into a specific position and can be performed according to a method as described, for example, in Molecular Cloning, 2nd. ed. or Current Protocols in Molecular Biology, Supplement 1 to 38, John Wiley & Sons (1987-1997).

The polyribonucleotide according to the present invention can be preferably exemplified by a polyribonucleotide which is of a single chain form as a primary structure and can be preferably exemplified by a polyribonucleotide having a cloverleaf structure containing a D arm, an anticodon arm, and a T arm as a secondary structure.

The lipofection reagent used in combination with the improving agent of the present invention is not particularly limited provided that the gene transfer efficiency-improving effect of the present invention is obtained, and can use a commercial lipofection reagent. The commercial lipofection reagent can be preferably exemplified by Fugene (registered trademark) HD transfection reagent (from Roche Applied Science), Lipofectamine (registered trademark) 2000 (from Invitrogen), Lipofectamine (registered trademark) LTX (from Invitrogen), Lipofectamine (registered trademark) LTX plus (from Invitrogen), JetPEI (registered trademark) (from Polyplus-transfection), GeneJuice (registered trademark) (from Takara Bio Inc.), and Turbofect (registered trademark) (from Fermentas), and among others, can be more preferably exemplified by Fugene (registered trademark) HD transfection reagent and Lipofectamine (registered trademark) 2000 since the gene transfer efficiency-improving effect of the present invention obtained using them is more excellent.

Preferred examples of the combination between tRNA and a lipofection reagent used in the present invention can include a combination between yeast-derived tRNA and Fugene (registered trademark) HD transfection reagent, a combination between calf liver-derived tRNA and Fugene (registered trademark) HD transfection reagent, a combination between wheat germ-derived tRNA and Fugene (registered trademark) HD transfection reagent, a combination between E. coli-derived tRNA and Fugene (registered trademark) HD transfection reagent, a combination between yeast-derived tRNA and Fugene (registered trademark) HD transfection reagent, a combination between calf liver-derived tRNA and Lipofectamine (registered trademark) 2000, a combination between wheat germ-derived tRNA and Lipofectamine (registered trademark) 2000, and a combination between E. coli-derived tRNA and Lipofectamine (registered trademark) 2000, and more preferred examples thereof can include a combination between yeast-derived tRNA and Fugene (registered trademark) HD transfection reagent and a combination between calf liver-derived tRNA and Fugene (registered trademark) HD transfection reagent, among others.

The method for using the improving agent of the present invention in combination with a lipofection reagent is not particularly limited provided that it is a method involving using the improvement agent of the present invention together with the lipofection reagent in a common lipofection method, and more specifically it is not particularly limited provided that when lipofection is performed, a step is included in which the improving agent of the present invention, a gene to be transferred, and the lipofection reagent together contact mammalian cells as a host; the step can be preferably exemplified by a step of adding and mixing the improving agent of the present invention, the gene to be transferred, and the lipofection reagent in a solvent such as distilled water to prepare a lipofection solution, which is then added to the mammalian cells.

The concentration of the improving agent of the present invention in using the improving agent of the present invention in combination with a lipofection reagent is not particularly limited provided that the gene transfer efficiency-improving effect of the present invention is obtained, and can be properly regulated depending on the type of tRNA and the type of host cells to be used; however, preferred examples thereof used can include 1 to 100 μg/mL, preferably 3 to 50 μg/mL, more preferably 5 to 25 μg/mL in terms of the concentration of tRNA in the lipofection solution. For the purpose of the present invention, the "concentration in the lipofection solution" means the concentration in a solution in a form in which the lipofection reagent and DNA are mixed (lipofection solution) used in lipofecting a target gene into host cells. The amount of the lipofection solution used in performing the lipofection can be exemplified by an amount in which the lipofection solution is diluted 5 to 15 times, preferably 7 to 13 times, more preferably 9 to 11 times, particularly preferably 10 times by adding the lipofection solution to a solution contacting host cells.

The mammalian cells as a host are not particularly limited provided that the gene transfer efficiency-improving effect of the present invention is obtained; however, it can be preferably exemplified by cells derived from a mammal such as a human, a monkey, a mouse, a rat, a hamster, a guinea pig, a cow, a pig, a horse, a rabbit, a sheep, a goat, a cat, or a dog, and among others, can be more preferably exemplified by cells derived from a human, a monkey, or a mouse. The human-derived cells can be preferably exemplified by 293 cells (ATCC CRL-1573) and HeLa cells (ATCC CCL-2); the monkey-derived cells can be preferably exemplified by COS7 cells (ATCC CRL-1651); and the mouse-derived cells can be preferably exemplified by NIH3T3 cells (ATCC CRL-1658) and EB5 cells (RIKEN BRC AES0151). These mammalian cells, for example, 293 cells, HeLa cells, and COS7 cells are available based on the above-described ATCC numbers from ATCC and EB5 cells are available from Institute of Physical and Chemical Research, Japan based on the above-described RIKEN number.

The target gene to be lipofected into mammalian cells is preferably operably positioned under the control of a promoter expressible in host cells. Here, the target gene being operably positioned under the control of the promoter means the promoter being linked with the target gene so that the promoter bind to a transcription factor to induce the expression of the target gene. The promoter can be preferably exemplified by human cytomegalovirus promoter (CMV promoter), SV40 initial promoter, SRα promoter, human elongation factor 1-α promoter, bovine growth hormone promoter, and β-actin gene promoter, and the like. The "target gene" may be any gene, and can be preferably exemplified by a useful protein gene encoding some useful protein. The useful protein gene can be preferably exemplified by genes of cytokines such as erythropoietin, genes encoding antibodies, and genes of virus vaccine proteins. The target gene and the promoter are preferably used by insertion into a vector replicable in host cells; the vector can be preferably exemplified by a plasmid replicable in host cells and can especially preferably exemplified by pCMV vector having CMV promoter.

Whether the target gene has been transferred to host cells can be easily confirmed by transferring a marker gene together with the target gene and identifying the expression of the marker gene in the transformant.

The improving agent of the present invention has the gene transfer efficiency-improving effect of the present invention. Whether a tRNA has the gene transfer efficiency-improving effect of the present invention can be easily confirmed, for example, by luciferase assay comprising the steps of: providing pCMV-GLuc which is a plasmid in which Gaussia-derived secretory luciferase (Gaussia Luciferase: GLuc) is positioned under the control of CMV (Cytomegalovirus) promoter; adding 0.5 μg of pCMV-GLuc, 0.1 to 10 μg of tRNA, and 1 μL of Fugene (registered trademark) HD transfection reagent (from Roche Applied Science) to 100 μL of distilled water, followed by allowing to stand at 28° C. for 30 minutes to prepare a lipofection solution; seeding 200 μL/well ($2 \times 10^3$ cells/well) of any one type of mammalian cells on a 96-well flat bottomed plate, followed by culture for 20 hours; removing the medium of each well and adding 180 μL/well each of new media; immediately thereafter, adding 20 μL of the above-described lipofection solution to each well to perform lipofection; measuring luciferase activity for each well after a lapse of 24 hours from the addition of the lipofection solution; and comparing the maximum value of the measured values (RLU (counts/sec/μL)) of the luciferase activity when 0.1 to 10 μg of the tRNA is used with the measured value (RLU (counts/sec/μL)) (control value) of the luciferase activity obtained by the same assay except for using no tRNA to determine the tRNA as having the gene transfer efficiency-improving effect of the present invention when the maximum value is higher than the control value. Here, the "maximum value" means the maximum value of the measured values (RLU (counts/sec/μL)) of the luciferase activity when the tRNA is used in amounts of 5 points or more (preferably 8 points or more) within the range from 0.1 to 10 μg, and can be more preferably exemplified by the maximum value of the measured values (RLU (counts/sec/μL)) of the luciferase activity when the tRNA is used in amounts of the 8 points of 0.1 μg, 0.2 μg, 0.3 μg, 0.5 μg, 1 μg, 2.5 μg, 5 μg, and 10 μg. The "any one type of mammalian cells" can be preferably exemplified by mammalian cells selected from NIH3T3 cells, COS7 cells, 293 cells, HeLa cells, and EB5 cells.

Examples of the preferred degree of the gene transfer efficiency-improving effect of the present invention preferably include that the maximum value (RLU (counts/sec/μL)) in the above luciferase assay is 2 times or more, preferably 3 times or more, more preferably 5 times or more, more preferably 7 times or more, more preferably 10 times or more, more preferably 15 times or more, more preferably 20 times or more, more preferably 30 times or more, more preferably 50 times, more preferably times or more to the control value (RLU (counts/sec/μL)).

The content of tRNA in the improving agent of the present invention is not particularly limited; however, the ratio of the tRNA according to the present invention to the improving agent of the present invention may be, for example, 0.1 to 100% by mass, preferably 0.5 to 90% by mass, more preferably 1 to 80% by mass.

The improving agent of the present invention preferably comprises a lipofection reagent in addition to tRNA. The improving agent of the present invention encompasses tRNA and a lipofection reagent contained in the same container and tRNA and a lipofection reagent contained in separate containers. The improving agent of the present invention may also comprise another efficiency improving agent for gene transfer to mammalian cells and optional ingredients such as polyethylene glycol (PEG) in addition to the tRNA of the present invention provided that the gene transfer efficiency-improving effect of the present invention is obtained.

The further combined use of polyethylene glycol is preferable because it can increase the gene transfer efficiency-improving effect of the present invention. The molecular weight of polyethylene glycol is not particularly limited; however, from the view point of increasing the gene transfer efficiency-improving effect of the present invention, it can be preferably exemplified by a molecular weight ranging from 2,000 to 6,000, can be more preferably exemplified by a molecular weight ranging from 3,000 to 5,000, and can be still more preferably exemplified by a molecular weight ranging from 3,000 to 4,000.

The usage amount of polyethylene glycol can be preferably exemplified by a concentration of 3 to 30% by mass in the lipofection solution, can be more preferably exemplified by 3 to 20% by mass, and can be still more preferably exemplified by 4 to 6% by mass. The usage amount of polyethylene glycol as another expression can be preferably exemplified by 300 to 1,000% by mass based on the lipofection reagent used, can be more preferably exemplified by 300 to 750% by mass, and can be still more preferably exemplified by 400 to 600% by mass.

The tRNA contained in the improving agent of the present invention may be properly formulated by an ordinary method. The dosage form of the formulation can be exemplified by solid formulations such as powders and liquid medicines such as solutions; however, it can be preferably exemplified by solid formulations since tRNA can be more stably preserved. When the tRNA according to the present invention is formulated, there may be blended proper carriers, for example, optional ingredients such as an excipient, a binder, a solvent, a solubilizer, a suspending agent, an emulsifier, an isotonizing agent, a buffering agent, a stabilizer, a preservative, an antioxidant, a lubricant, a wetting agent, and a diluent as needed for formulation. The efficiency improving agent for gene transfer to mammalian cells of the present invention can also be expressed as the agent for gene transfer to mammalian cells of the present invention.

2. Method for Improving Efficiency of Gene Transfer to Mammalian Cell of Present Invention The method for improving efficiency of gene transfer to mammalian cells of the present invention is characterized by using tRNA in combination with a lipofection reagent. The method for using tRNA in combination with a lipofection reagent can be preferably exemplified by the same method as the above-described method for using the improving agent of the present invention in combination with a lipofection reagent. According to the method for improving efficiency of gene transfer to mammalian cells of the present invention, efficiency of gene transfer to mammalian cells can be prominently improved. The method for improving efficiency of gene transfer to mammalian cells of the present invention can also be expressed as the method for gene transfer to mammalian cells of the present invention.

3. Method for Transforming Mammalian Cell of Present Invention

The method for transforming mammalian cells of the present invention is characterized in that tRNA is used in combination with a lipofection reagent to lipofect a target gene into mammalian cells. The method for using tRNA in combination with a lipofection reagent can be preferably exemplified by the same method as the above-described method for using the improving agent of the present invention in combination with a lipofection reagent. According to the method for transforming mammalian cells of the present invention, the transformation in mammalian cells can be performed with high efficiency.

Example 1

Influence of tRNA on Gene Transfer Efficiency

To examine the influence of tRNA on gene transfer efficiency, the following lipofection experiment was performed.

pCMV-GLuc (from New England BioLab) was first provided as a reporter plasmid. In the pCMV-GLuc, a gene encoding Gaussia-derived secretory luciferase (Gaussia Luciferase: GLuc) is positioned under the control of CMV (Cytomegalovirus) promoter. The CMV promoter is suitable for the preparation of a reporter plasmid for the lipofection experiment because it is a promoter constitutively expressed in mammalian cells.

Calf liver-derived tRNA (from Sigma Aldrich, "Ribonucleic acid, transfer Type VI From Bovine liver", Cat#R4752-50UN) and total RNA (from Sigma Aldrich, "Ribonucleic acid from calf liver Type IV", Cat#R7250-100MG) were then provided. Almost all of the total RNA consist of rRNA. Subsequently, 0.5 µg of pCMV-GLuc and a predetermined amount of RNA (tRNA or total RNA) were added to each 100 µL of distilled water. To the solution was added 1 µL of Fugene (registered trademark) HD transfection reagent (from Roche Applied Science) as a lipofection reagent to a total volume of 10 µL. The solution was allowed to stand at 28° C. for 30 minutes. This solution (hereinafter, also indicated as "lipofection solution") was prepared in a total volume of about 404 µL. The above-described predetermined amount was 0 µg, 0.078 µg, 0.156 µg, 0.313 µg, 0.625 µg, 1.25 µg, 2.5 µg, 5 µg, or 10 µg when RNA is tRNA or total RNA (0 µg/mL, 10.78 µg/mL, 21.56 µg/mL, 33.13 µg/mL, 56.25 µg/mL, 1,012.5 µg/mL, 25 µg/mL, 50 µg/mL, or 100 µg/mL, respectively in terms of the concentration in the lipofection solution).

NIH3T3 (NIH-3T3) cells as cultured cells isolated from mouse fetal skin were provided, seeded in an amount of 200 µL/well ($2 \times 10^3$ cells/well) on a 96-well bottomed plate containing a medium (a medium in which 10% FCS was admixed with RPMI1640) and cultured for 20 hours. Then, the medium of each well was removed, and 180 µL/well of a new medium (a medium in which 10% FCS was admixed with RPMI1640) was added. Immediately thereafter, 20 µL of the above-described lipofection solution was added to each well for lipofection. Luciferase activity was measured for each well 24 hours after adding the lipofection solution. The results are shown in FIG. 1.

Figure 1:
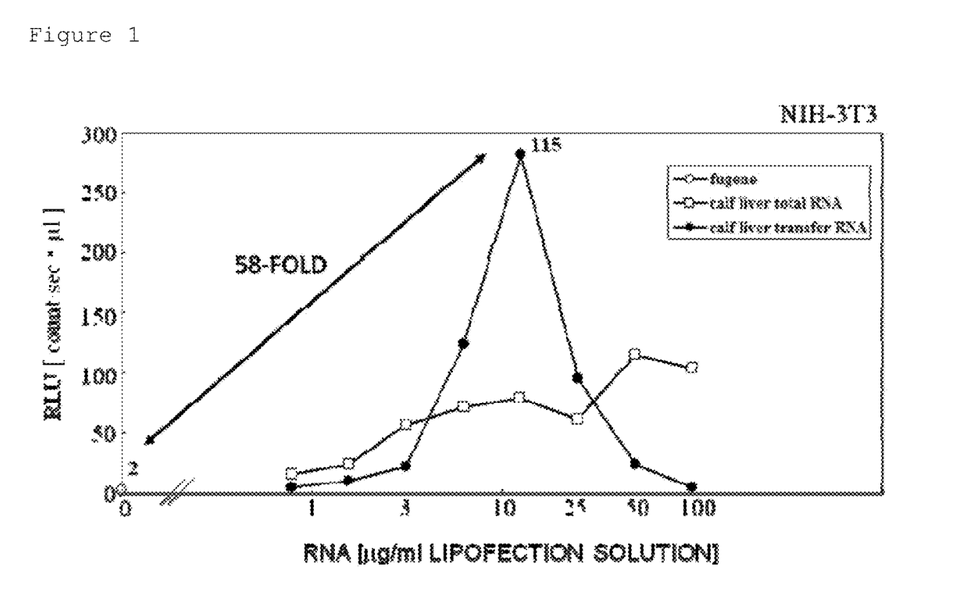
FIG. 1 is a graph showing the results of "Example 1: Influence of tRNA on Gene Transfer Efficiency".

The results of FIG. 1 showed that the use of 0.5 to 2.5 µg (5 to 25 µg/mL in terms of the concentration in the lipofection solution) of tRNA in combination with the lipofection reagent dramatically increased gene transfer efficiency compared to the combined use of total RNA and the lipofection reagent. Particularly, the use of 1.25 µg (12.5 µg/mL in terms of the concentration in the lipofection solution) of tRNA increased gene transfer efficiency 58-fold compared to no use of RNA (control).

Example 2

Effect of tRNA Derived from Various Organism Species

In Example 1, mouse-derived cells were used as host cells and calf-derived tRNA was used. To examine whether even the use of another mammalian cells as host cells and tRNA derived from a different organism species had the effect of improving gene transfer efficiency, the following lipofection experiment was performed.

As tRNA, in addition to calf liver-derived tRNA, there were provided yeast-derived tRNA (from Sigma Aldrich, "Ribonucleic acid, Type X-SA transfer from baker's yeast", Cat#R8759-100UN), wheat germ-derived tRNA (from Sigma Aldrich, "Ribonucleic acid, Type V, transfer from Wheat Germ", Cat#R7876-500UN), *E. coli*-derived tRNA (from Sigma Aldrich, "Ribonucleic acid, transfer Type XX from *Escherichia coli* strain W", Cat#R1753-100UN). COS7 cells as monkey kidney-derived cultured cells were provided as host cells. The lipofection experiment was carried out in the same way as the lipofection experiment in Example 1 except for using COS7 cells in place of NIH3T3 cells and using tRNA derived from various organism species as tRNA. As control, the lipofection experiment was also carried out by a method using no tRNA. These results are shown in FIG. 2.

Figure 2:
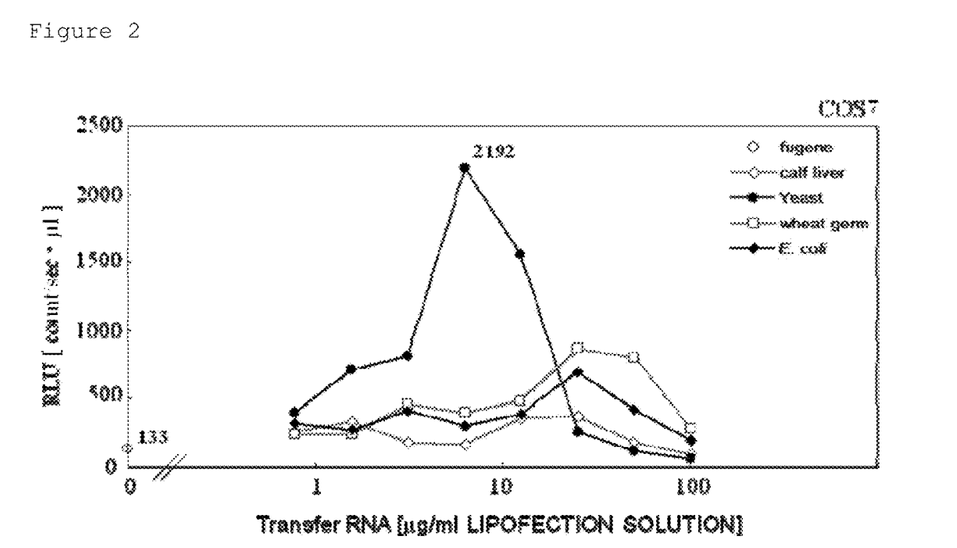
FIG. 2 is a graph showing the results of "Example 2: Effect of tRNA Derived from Various Organism Species".

The results of FIG. 2 showed that the use of tRNA derived from any of the organism species in combination with the lipofection reagent was observed to have the effect of improving efficiency of gene transfer, to one degree or another, compared to no use of tRNA (fugene: control). Specifically, it was calculated how many times the maximum value of gene transfer efficiency in the tRNA concentration of 1 to 100 µg/mL in the lipofection solution was larger than the value of control gene transfer efficiency; as a result, it was 2.8 times for the calf liver-derived tRNA, 16.5 times for the yeast-derived tRNA, 6.5 times for the wheat germ-derived tRNA, and 5.2 times for the *E. coli*-derived tRNA. The gene transfer efficiency was especially improved for 0.5 to 2.5 µg (5 to 25 µg/mL in terms of the concentration in the lipofection solution) of the yeast-derived tRNA and for 1.25 to 5 µg (12.5 to 50 µg/mL in terms of the concentration in the lipofection solution) of each of other derived tRNAs.

Example 3

Dependency of Effect on Type of Lipofection Reagent

In Examples 1 and 2, Fugene (registered trademark) HD transfection reagent (from Roche Applied Science) was used as a lipofection reagent. Accordingly, to examine whether the tRNA's effect of improving gene transfer efficiency was obtained even when a different lipofection reagent was used, the following lipofection experiment was carried out.

The lipofection experiment was performed in the same way as the lipofection experiment in Example 2 except for using Fugene (registered trademark) HD transfection reagent, Lipofectamine (registered trademark) 2000 (from Invitrogen), Lipofectamine (registered trademark) LTX (from Invitrogen), Lipofectamine (registered trademark) LTX plus (from Invitrogen), JetPEI (registered trademark) (from Polyplus-transfection), GeneJuice (registered trademark) (from Takara Bio Inc.), or Turbofect (registered trademark) (from Fermentas) as a lipofection reagent and using 0.625 μg (6.25 μg/mL in terms of the concentration in the lipofection solution) of yeast-derived tRNA (from Sigma Aldrich, "Ribonucleic acid, Type X-SA transfer from baker's yeast", Cat#R8759-100UN) as tRNA. As control, the lipofection experiment was also carried out by a method using no tRNA. These results are shown in FIG. 3.

Figure 3:
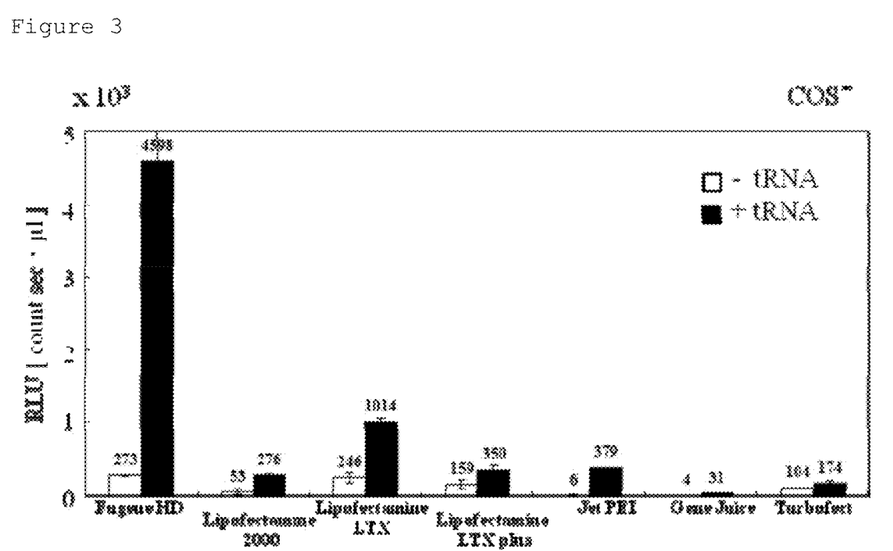
FIG. 3 is a graph showing the results of "Example 3: Dependency of Effect on Type of Lipofection Reagent".

The results of FIG. 3 showed that each of the lipofection reagents also dramatically improved gene transfer efficiency when used in combination with the tRNA. Among others, Fugene (registered trademark) HD transfection reagent and Lipofectamine (registered trademark) 2000 markedly improved the gene transfer efficiency.

Example 4

Dependency of Effect on Type of Host Cell

NIH3T3 cells were used as host cells in Example 1 and COS7 cells were used as host cells in Examples 2 to 3. Accordingly, to examine whether the tRNA's effect of improving gene transfer efficiency was obtained even when different mammalian cells was used as host cells, the following lipofection experiment was carried out.

The lipofection experiment was performed in the same way as the lipofection experiment in Example 2 except for using NIH3T3 cells, COS7 cells, 293 cells, or HeLa cells as host cells and using yeast-derived tRNA (from Sigma Aldrich, "Ribonucleic acid, Type X-SA transfer from baker's yeast", Cat#R8759-100UN) over a range of concentrations as tRNA. As control, the lipofection experiment was also carried out by a method using no tRNA. These results are shown in FIG. 4. 293 Cells are human fetal kidney-derived cultured cells, and HeLa cells are human cervical cancer-derived cultured cells.

Figure 4:
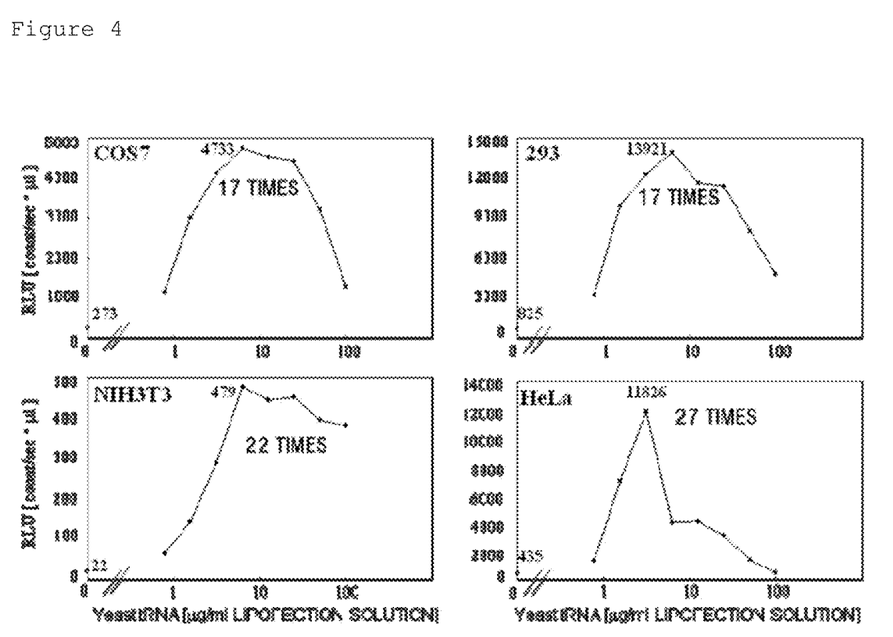
FIG. 4 is a series of graphs showing the results of "Example 4: Dependency of Effect on Type of Host Cell".

The results of FIG. 4 showed that the use of tRNA in combination therewith also dramatically improved gene transfer efficiency when all the mammalian cells were each used. Specifically, the maximum value was 17 times the control value for COS7 cells; the maximum value was 17 times the control value for 293 cells; the maximum value was 22 times the control value for NIH3T3 cells; and the maximum value was 27 times the control value for HeLa cells.

Example 5

Synergistic Effect of Addition of PEG to Lipofection Reagent and tRNA

To examine the influence of the use of PEG in addition to a lipofection reagent and tRNA, the following lipofection experiment was carried out.

The lipofection experiment was performed in the same way as the lipofection experiment in Example 2 except for using 0.625 μg (6.25 μg/mL in terms of the concentration in the lipofection solution) of yeast-derived tRNA (from Sigma Aldrich, "Ribonucleic acid, Type X-SA transfer from baker's yeast", Cat#R8759-100UN) as tRNA, using 293 cells or HeLa cells as mammalian cells, and further adding PEG3350 (from Sigma) to 5% by mass to the lipofection solution. The lipofection experiment was also carried out by a method using no PEG3350. In addition, as control, the lipofection experiment was also carried out by a method using no tRNA and by a method using no tRNA but using PEG3350. These results are shown in FIG. 5.

Figure 5:
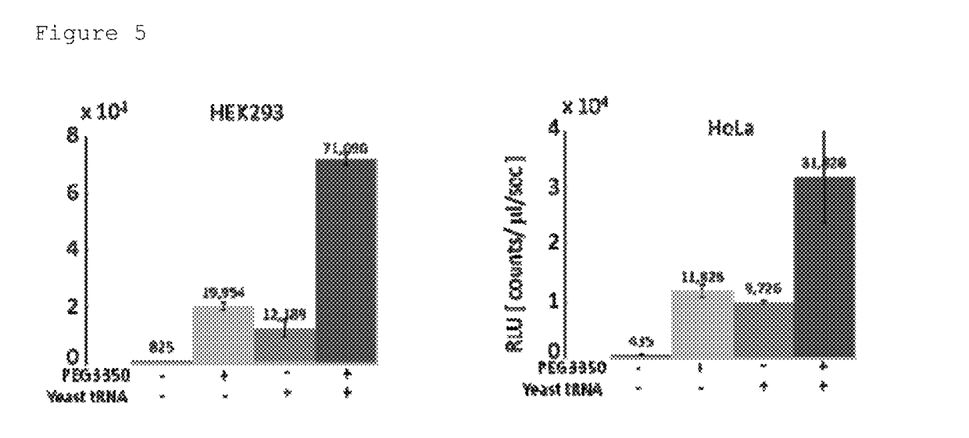
FIG. 5 is a pair of graphs showing the results of "Example 5: Synergistic Effect of Addition of PEG to Lipofection Reagent and tRNA". The left graph shows the results obtained using HEK293 cells and the right graph shows the results obtained using HeLa cells.

FIG. 5 showed that the further use of PEG in addition to "the lipofection reagent and tRNA" synergistically further improved gene transfer efficiency. Specifically, the further use of PEG in addition to "the lipofection reagent and tRNA" increased gene transfer efficiency about 5.9-fold when the host cells were 293 cells and increased the gene transfer efficiency about 3.3-fold when the host cells were HeLa cells.

Figure 6:
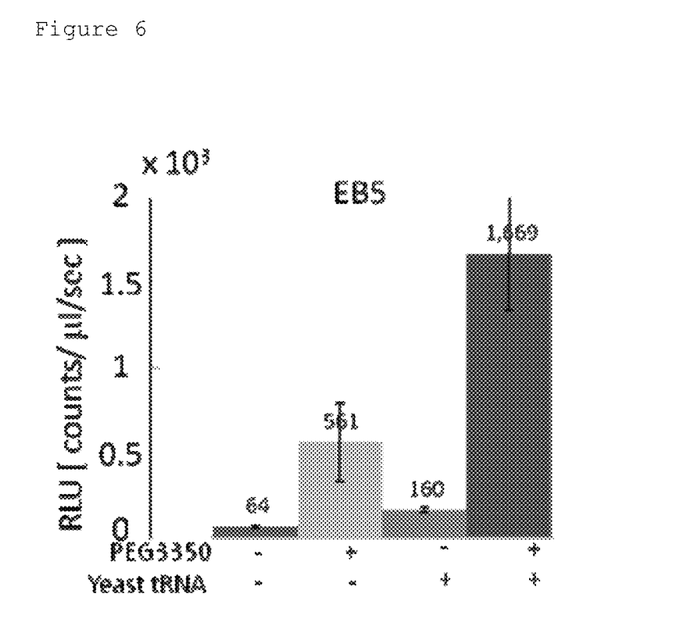
FIG. 6 is a graph showing the results of "Synergistic Effect of Addition of PEG to Lipofection Reagent and tRNA". The figure shows the results obtained using EB5 cells.

The lipofection experiment performed in FIG. 5 above was also similarly carried out in mouse E14tg2a cell-derived ES cells, that is, EB5 cells. FIG. 6 showed that the further use of PEG in addition to "the lipofection reagent and tRNA" synergistically further improved gene transfer efficiency. Specifically, the further use of PEG in addition to "the lipofection reagent and tRNA" increased gene transfer efficiency in EB5 cells about 10-fold.

Reference Example 1

Effect of Addition of PEG to Lipofection Reagent

To examine the influence of the addition of PEG to a lipofection reagent without using tRNA and the influence of the molecular weight of PEG, the following lipofection experiment was carried out.

The lipofection experiment was performed in the same way as the lipofection experiment in Example 2 except for using no tRNA and adding 0 to 30% (w/v) (0 to 3% (w/v) in terms of the concentration in a lipofection solution) of PEG of each of various molecular weights (600, 1,000, 3,350, 6,000, or 10,000) in terms of the concentration in the lipofection solution. These results are shown in FIG. 7.

Figure 7:
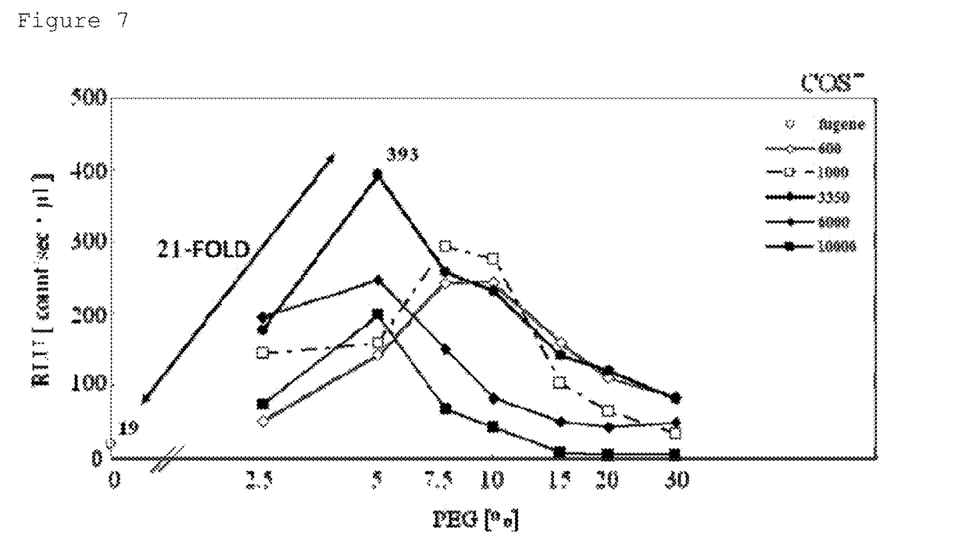
FIG. 7 is a graph showing the results of "Reference Example 1: Effect of Addition of PEG to Lipofection Reagent".

The results of FIG. 7 showed that the use of PEG of any of the molecular weights in combination with the lipofection reagent was observed to have the effect of improving efficiency of gene transfer, to one degree or another, compared to no use of PEG (fugene: control). Among others, PEG of a molecular weight of 3,350 increased gene transfer efficiency as much as 21-fold compared to control when the concentration thereof in the lipofection solution was 5% (w/v).

Reference Example 2

Influence of Type of Lipofection Reagent

In Reference Examples 1 and 2, Fugene (registered trademark) HD transfection reagent (from Roche Applied Science) was used as a lipofection reagent. Accordingly, to examine whether the PEG's effect of improving gene transfer efficiency was obtained even when a different lipofection reagent was used, the following lipofection experiment was carried out.

The lipofection experiment was performed in the same way as the lipofection experiment in Reference Example 1 except for using Fugene (registered trademark) HD transfection reagent, Lipofectamine (registered trademark) 2000 (from Invitrogen), Lipofectamine (registered trademark) LTX (from Invitrogen), Lipofectamine (registered trademark) LTX plus (from Invitrogen), Carri Gene (from Nitto Denko Tech. Corp.), JetPEI (registered trademark) (from Polyplus-transfection), GeneJuice (registered trademark) (from Takara Bio Inc.), or Turbofect (registered trademark) (from Fermentas) as a lipofection reagent and using 5% (w/v) of PEG of a molecular weight of 3,350 as PEG. As control, the lipofection experiment was also carried out by a method using no PEG. These results are shown in FIG. 8.

Figure 8:
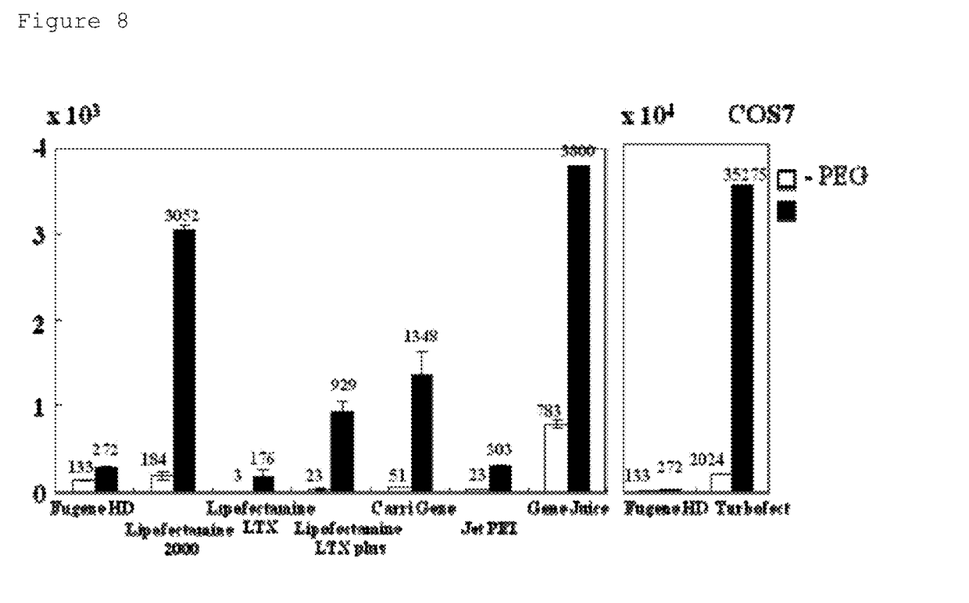
FIG. 8 is a graph showing the results of "Reference Example 2: Influence of Type of Lipofection Reagent".

The results of FIG. 8 showed that each of the lipofection reagents also markedly improved gene transfer efficiency when used in combination with the PEG.

Reference Example 3

Influence of Type of Host Cell

In Reference Examples 1 and 2, COS7 cells were used as host cells. Accordingly, to examine whether the PEG's effect of improving gene transfer efficiency was obtained even when different mammalian cells was used as host cells, the following lipofection experiment was carried out.

The lipofection experiment was performed in the same way as the lipofection experiment in Reference Example 1 except for using COS7 cells, NIH3T3 cells, 293 cells, or HeLa cells as host cells and using 5% (w/v) of PEG of a molecular weight of 3,350 as PEG. As control, the lipofection experiment was also carried out by a method using no PEG. These results are shown in FIG. 9.

Figure 9:
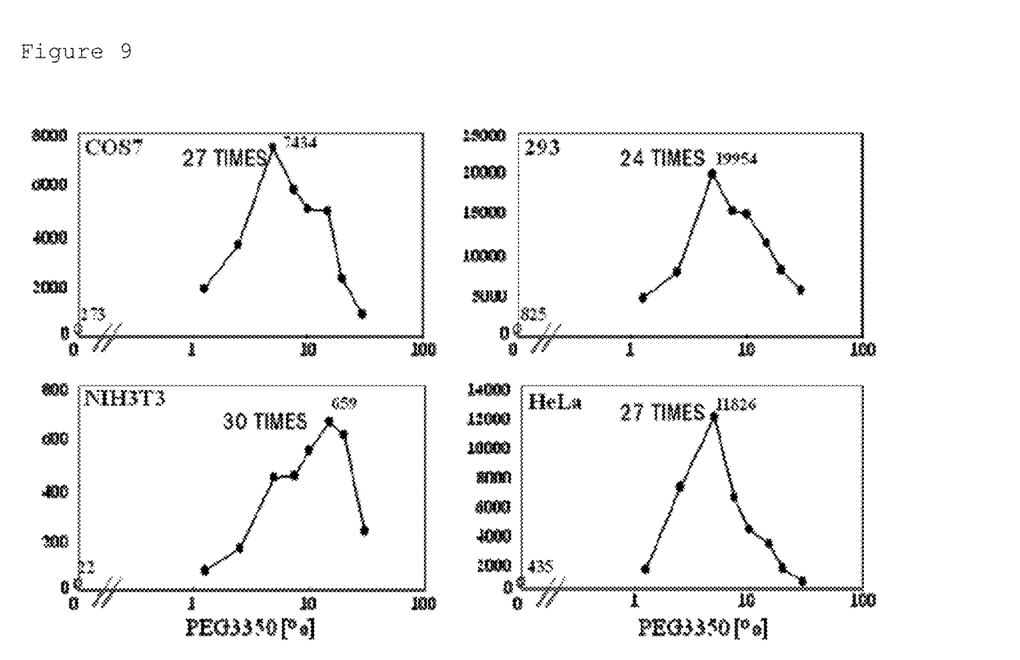
FIG. 9 is the results of "Reference Example 3: Influence of Type of Host Cell".

The results of FIG. 9 showed that the use of PEG in combination therewith also markedly improved gene transfer efficiency when all the mammalian cells were each used. Specifically, the maximum value was 27 times the control value for COS7 cells; the maximum value was 24 times the control value for 293 cells; the maximum value was 30 times the control value for NIH3T3 cells; and the maximum value was 27 times the control value for HeLa cells.

INDUSTRIAL APPLICABILITY

The present invention can be suitably used in the field of gene transfer to mammalian cells.

```
                        SEQUENCE LISTING

<160> NUMBER OF SEQ ID NOS: 4

<210> SEQ ID NO 1
<211> LENGTH: 85
<212> TYPE: RNA
<213> ORGANISM: Bovine
<220> FEATURE:
<223> OTHER INFORMATION: Leucine-tRNA
<220> FEATURE:
<223> OTHER INFORMATION: Inventor: Akada, Rinji
      Inventor: Nakamura, Mikiko

<400> SEQUENCE: 1
gguagcgugg ccgagcgguc uaaggcgcug gauugaggcu ccagucucuu cggggggcgug      60 gguucgaauc ccaccgcugc cacca                                            85

<210> SEQ ID NO 2
<211> LENGTH: 197
<212> TYPE: RNA
<213> ORGANISM: Saccharomyces cerevisiae
<220> FEATURE:
<223> OTHER INFORMATION: Leucine-tRNA

<400> SEQUENCE: 2
cugaggauuc ggguaaaaua ggguauuuaa cugguuaccg gaaagguuua gaaaauucgu      60 ggagguugg ccgagcgguc uaaggcggca gacuuaagau cuguuggacg guuguccgcg      120
cgaguucgaa ccucgcaucc uucaguauuu uuuuugauga uuuaacguac uauuaacuag      180
aauaauaggg aaaugca                                                     197

<210> SEQ ID NO 3
<211> LENGTH: 76
<212> TYPE: RNA
<213> ORGANISM: Wheat
<220> FEATURE:
<223> OTHER INFORMATION: Phenylalanine-tRNA

<400> SEQUENCE: 3
gcggggauag cucaguuggg agagcgucag acugaagauc ugaaggucgc guguucgauc      60
cacgcucacc gcacca                                                     76

<210> SEQ ID NO 4
<211> LENGTH: 300
<212> TYPE: RNA
<213> ORGANISM: Escherichia coli
```

-continued

```
<220> FEATURE:
<223> OTHER INFORMATION: Leucine-tRNA

<400> SEQUENCE: 4
auucuucauc aucagucugg ugcuggguaa caucaauagc aacaaaacca auaaagguag      60
cgaaugggaa aaucugagug caccggcgaa aaccgaacaa acucagccag cugcuccggc     120
uaagccgacc agcgauaucc cgaacuaaaa aguaguaucc gugccgaggu gguggaauug     180
guagacacgc uaccuugagg ugguagugcc caauagggcu uacggguuca aguccegucc    240 ucgguaccaa auuccagaaa agagacgcug aaaagcgucu uuuuucguuu ugguccuggu     300
```

The invention claimed is:

1. A method for improving efficiency of gene transfer to mammalian cells in vitro, comprising the following steps (a) to (c) sequentially:
   (a) a step of mixing DNA comprising a target gene with transfer RNA (tRNA);
   (b) a step of adding a lipofection reagent to the mixture solution prepared in the step (a); and
   (c) a step of adding the lipofection solution prepared in the step (b) into mammalian cells in vitro.

2. The method according to claim 1, wherein polyethylene glycol is used in combination in step (b).

3. The method according to claim 1, wherein the concentration of tRNA in the lipofection solution ranges from 3 to 50 µg/mL in step (b).

4. The method according to claim 2, wherein the polyethylene glycol has a molecular weight ranging from 2,000 to 6,000.

5. The method according to claim 2, wherein the polyethylene glycol has a molecular weight ranging from 3,000 to 5,000.

* * * * *